(12) United States Patent
Thomas et al.

(10) Patent No.: US 6,964,665 B2
(45) Date of Patent: Nov. 15, 2005

(54) VERTEBRAL ALIGNMENT SYSTEM

(76) Inventors: James C. Thomas, 1005 Championship Way, Las Vegas, NV (US) 89134; Rick D. Roberts, 1121 Ox Rd., Trinidad, CA (US) 95570

(\*) Notice: Subject to any disclaimer, the term of this patent is extended or adjusted under 35 U.S.C. 154(b) by 436 days.

(21) Appl. No.: 10/036,235

(22) Filed: Dec. 27, 2001

(65) Prior Publication Data

US 2002/0087159 A1 Jul. 4, 2002

Related U.S. Application Data

(60) Provisional application No. 60/258,963, filed on Dec. 29, 2000.

(51) Int. Cl.$^7$ .............................................. A61B 17/58
(52) U.S. Cl. ...................................................... 606/61
(58) Field of Search ........................... 606/61, 72, 73

(56) References Cited

U.S. PATENT DOCUMENTS

| | | | |
|---|---|---|---|
| 3,579,831 A | * | 5/1971 | Stevens et al. .............. 433/174 |
| 3,741,205 A | * | 6/1973 | Markolf et al. ................ 606/61 |
| 4,463,753 A | | 8/1984 | Gustilo |
| 4,763,644 A | * | 8/1988 | Webb ........................... 606/61 |
| 5,000,165 A | | 3/1991 | Watanabe |
| 5,030,220 A | | 7/1991 | Howland |
| 5,100,405 A | | 3/1992 | McLaren |
| 5,139,499 A | | 8/1992 | Small et al. |
| 5,196,016 A | * | 3/1993 | Buser et al. ................... 606/72 |
| 5,217,497 A | | 6/1993 | Mehdian |
| 5,219,349 A | | 6/1993 | Krag et al. |
| 5,306,275 A | | 4/1994 | Bryan |
| 5,409,486 A | * | 4/1995 | Reese ........................... 606/73 |
| 5,425,733 A | * | 6/1995 | Schmieding ................. 606/104 |
| 5,437,671 A | | 8/1995 | Lozier et al. |
| 5,591,165 A | | 1/1997 | Jackson |
| 5,607,425 A | | 3/1997 | Rogozinski |
| 5,674,224 A | * | 10/1997 | Howell et al. ................. 606/88 |
| 5,713,900 A | * | 2/1998 | Benzel et al. .................. 606/61 |
| 5,743,912 A | * | 4/1998 | Lahille et al. ................. 606/65 |
| 5,885,299 A | | 3/1999 | Winslow et al. |
| 5,947,965 A | | 9/1999 | Bryan |
| 5,971,987 A | | 10/1999 | Huxel et al. |
| 5,984,922 A | | 11/1999 | McKay |
| 5,989,250 A | | 11/1999 | Wagner et al. |
| 6,001,098 A | | 12/1999 | Metz-Stavenhagen et al. |
| 6,004,322 A | | 12/1999 | Bernstein |
| 6,015,409 A | | 1/2000 | Jackson |
| 6,050,997 A | | 4/2000 | Mullane |
| 6,056,753 A | | 5/2000 | Jackson |
| 6,074,423 A | | 6/2000 | Lawson |
| 6,077,267 A | | 6/2000 | Huene |
| 6,110,173 A | | 8/2000 | Thomas, Jr. |
| 6,126,662 A | * | 10/2000 | Carmichael et al. ........... 606/72 |
| 6,132,430 A | | 10/2000 | Wagner |
| 6,139,548 A | | 10/2000 | Errico |
| 6,423,062 B2 | * | 7/2002 | Enayati ......................... 606/59 |

OTHER PUBLICATIONS

GMReis Implantes advertisement, "EXACTO for Polyaxial Pedicle Pin Stabilization System", no date.

\* cited by examiner

*Primary Examiner*—Eduardo C. Robert
(74) *Attorney, Agent, or Firm*—Christie, Parker & Hale, LLP

(57) ABSTRACT

A method and apparatus for aligning and fixing vertebral bodies is provided. The vertebral alignment system of the current invention comprises an integrated system of alignment rods, cannulated pedicle screws, filler plugs and fixation hardware. The components are designed such that a surgeon can accurately manipulate and align vertebral bodies using the removable alignment rods attached to the cannulated pedicle screws and to enable the installation of fixation system hardware while the alignment rods are still in place. A system and method for aligning vertebral bodies using the vertebral alignment system of the invention is also provided.

12 Claims, 14 Drawing Sheets

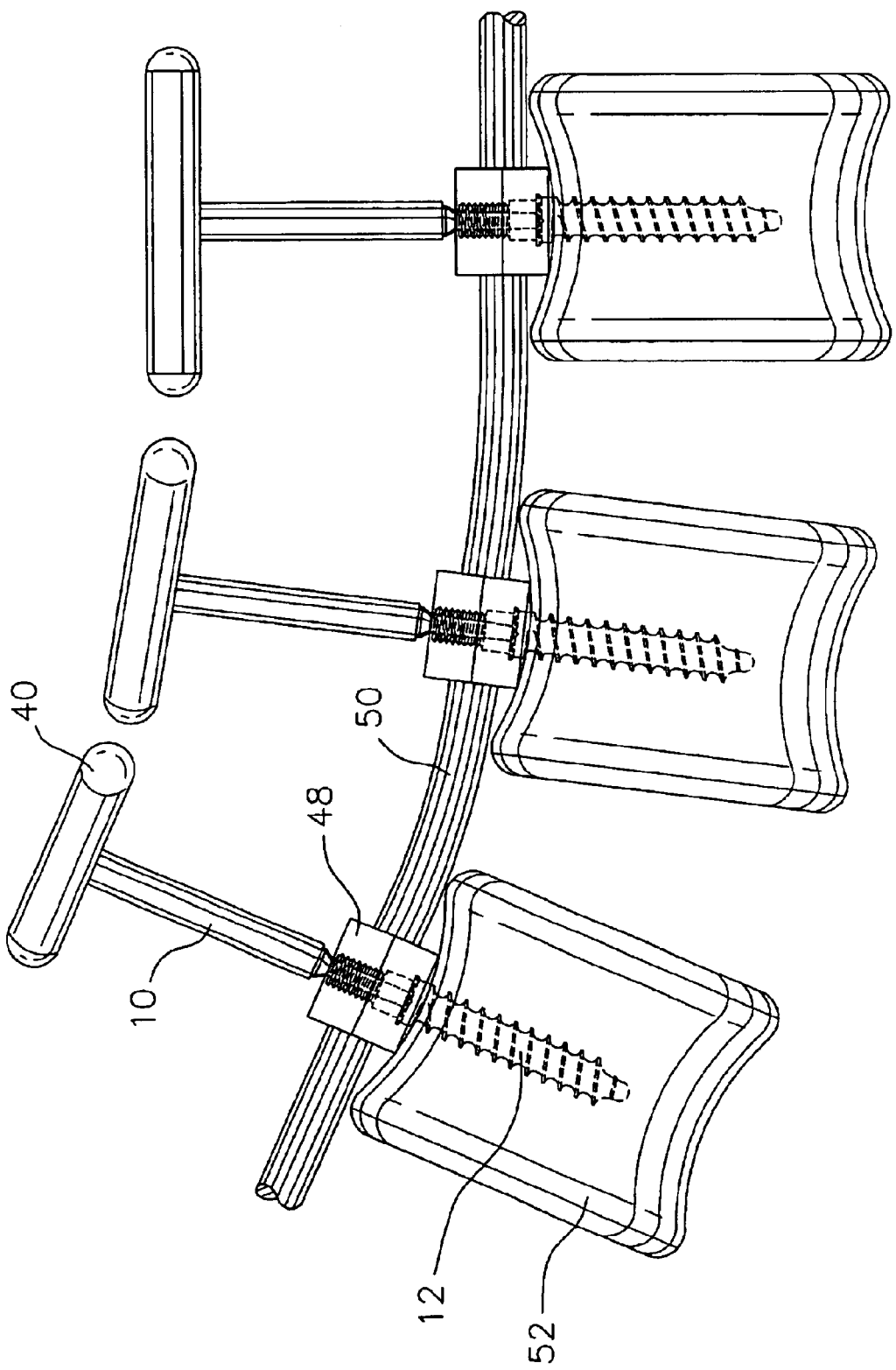

POSITIVE 0 NEGATIVE

VERTEBRAL ALIGNMENT SYSTEM

CROSS-REFERENCE TO RELATED APPLICATION

This application is based on provisional patent application Ser. No. 60/258,963, filed Dec. 29, 2000.

FIELD OF THE INVENTION

The present invention relates generally to a method and apparatus for alignment and fixation of vertebral bodies.

BACKGROUND OF THE INVENTION

Pedicle screws allow spine surgeons to attach rods or plates to the thoracic and lumbar spine. This rigidly immobilizes the spine segments, promoting the bone graft to grow into a fusion, welding spinal segments into one solid unit, reducing pain and stabilizing deformity.

Three types of deformity that spinal surgeons attempt to correct with regularity are Scoliosis, Spondylolisthesis, and Kyphosis, or flat back syndrome. Actual manipulation of the spine and correction of these thoracic and lumbar deformities is accomplished by distraction or compression of the points of attachment to the spine. Points of attachments are generally either hooks underneath the lamina, hooks under the pedicles or pedicle screws.

While many different pedicle screws have been developed, presently the pedicle screw is not considered a navigational point of attachment to the spine, nor have the prior art systems allowed for the attachment of the fixation hardware without first removing the alignment rods or cages.

For example, Krag, U.S. Pat. No. 5,219,349, which is incorporated herein by reference, discloses a method of aligning vertebral bodies utilizing a stabilization cage, but does not provide a system for attaching the fixation hardware to the pedicle screw while the alignment cage is in place. Likewise, Bernstein, U.S. Pat. No. 6,004,322, which is incorporated herein by reference, discloses a cannulated pedicle screw design utilized to fix the spine, but also does not provide a system for attaching alignment rods or for attaching fixation hardware while such alignment rods are in place.

With these current systems, the surgeon must remove the alignment device prior to securing the fixation hardware, allowing the vertebral bodies time to return to their improper original alignment. Accordingly, a need exists for a system and apparatus that allows a surgeon to accurately manipulate and align vertebral bodies and to enable the installation of a fixation system while such alignment devices are still in place.

SUMMARY OF THE INVENTION

The present invention relates generally to a method and apparatus for aligning and fixing vertebral bodies. More specifically, the present invention is directed to a system and method to allow a surgeon to accurately manipulate and align vertebral bodies using removable alignment rods attached to pedicle screws and to enable the installation of fixation system hardware while the alignment rods are still in place.

In one embodiment, the vertebral alignment system of the current invention consists of three main components: alignment rods, cannulated pedicle screws, and, optionally, filler plugs. In this embodiment, two pedicle screws, two alignment rods and, optionally, two filler plugs are used at each vertebral level to be aligned. The number of components used would depend upon the spinal abnormality and the number of vertebral bodies, or levels to be aligned and fused.

In a preferred embodiment the vertebral alignment system of the present invention is designed to work on "top loading" fixation systems, such as the Advanced Spine Verigrip system, although other types of fixation systems could be used. A top loading system provides for the pedicle screw bolts and hardware to be installed from the top of the pedicle screw.

In another preferred embodiment, the invention is directed to a system for aligning vertebral bodies comprising a multiplicity of vertebral alignment components as described above attached at suitable points of attachment as determined by the deformity of the spine.

In still another embodiment, the invention is directed to a method for aligning vertebral bodies. The method comprises manipulating, aligning and fixing the spine using a vertebral alignment system as described above.

In all of the above embodiments, it is preferred that the components of the system are made from an orthopaedically suitable material, such as, for example, stainless steel or titanium.

BRIEF DESCRIPTION OF THE DRAWINGS

These and other features and advantages of the present invention will be better understood by reference to the following detailed description when considered in conjunction with the accompanying drawings wherein:

FIG. 7c is a side view of an embodiment of fixation hardware according to the invention.

DETAILED DESCRIPTION OF THE INVENTION

Figure 1A:
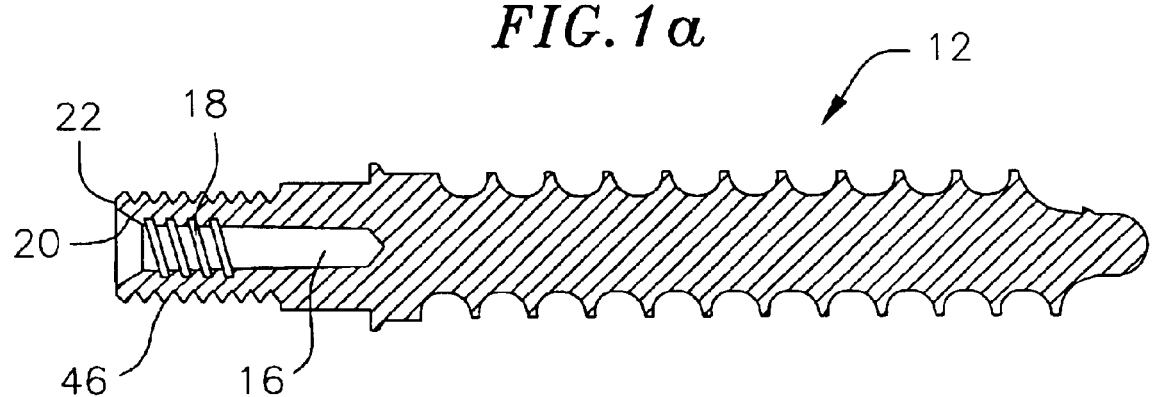
FIG. 1a is a side view and partial cross section of an embodiment of a pedicle screw according to a first embodiment of the invention.
Figure 1B:
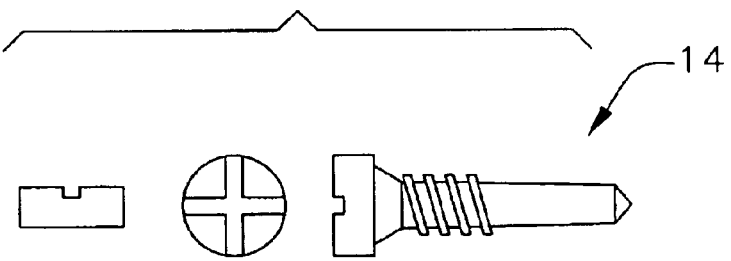
FIG. 1b is a front and side view of an embodiment of a filler screw according to the first embodiment of the invention.
Figure 1C:
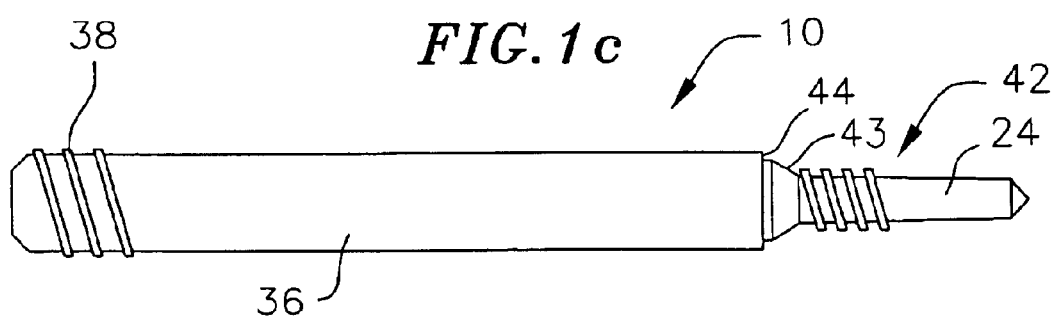
FIG. 1c is a side view of an embodiment of an alignment rod according to the first embodiment of the invention.
Figure 2A:
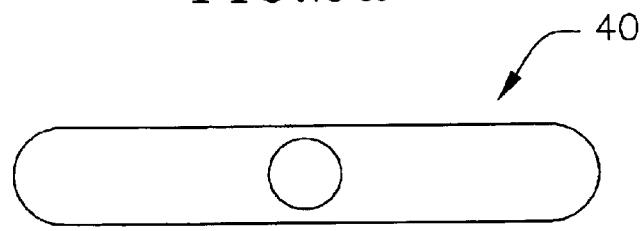
FIG. 2a is a front view of an embodiment of an alignment handle according to the first embodiment of the invention.
Figure 2B:
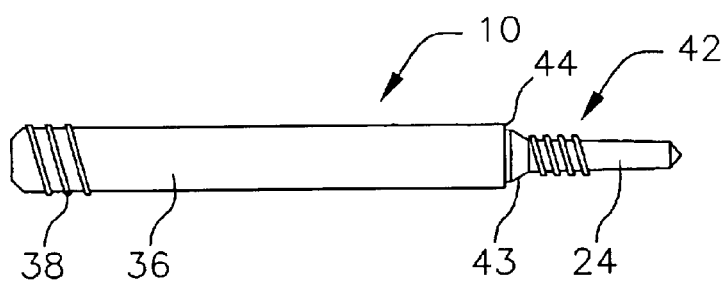
FIG. 2b is a side view of an embodiment of an alignment rod according to the first embodiment of the invention.
Figure 2C:
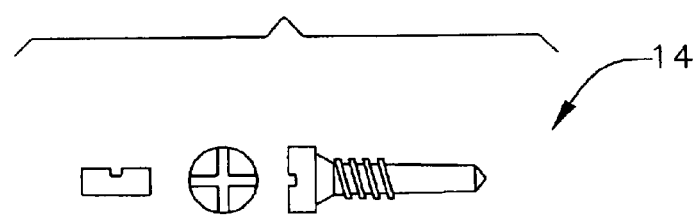
FIG. 2c is a front and side view of an embodiment of a filler screw according to the first embodiment of the invention.
Figure 2D:
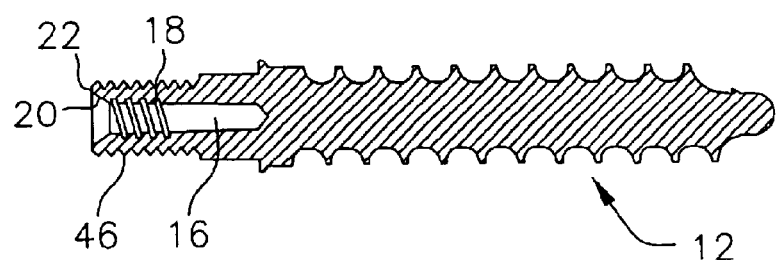
FIG. 2d is a side view and partial cross section of an embodiment of a pedicle screw according to the first embodiment of the invention.
Figure 3A:
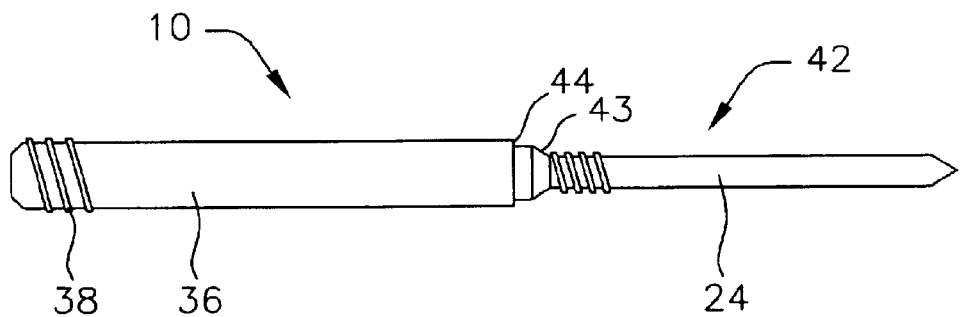
FIG. 3a is a side view of an embodiment of an alignment rod according to a second embodiment of the invention.
Figure 3B:
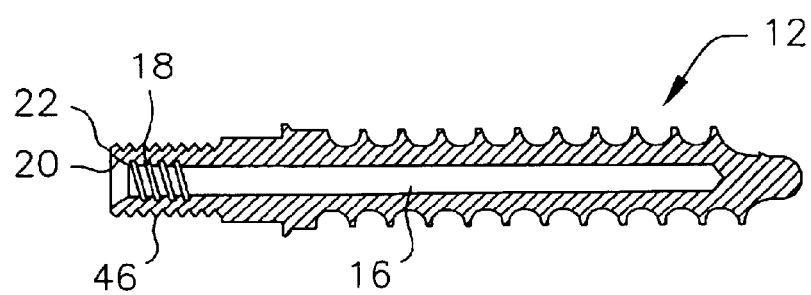
FIG. 3b is a side view and partial cross section of an embodiment of a pedicle screw according to the second embodiment of the invention.
Figure 3C:
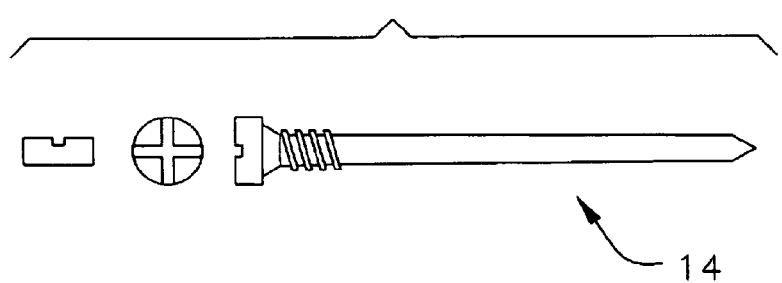
FIG. 3c is a front and side view of an embodiment of a filler screw according to the second embodiment of the invention.
Figure 3D:
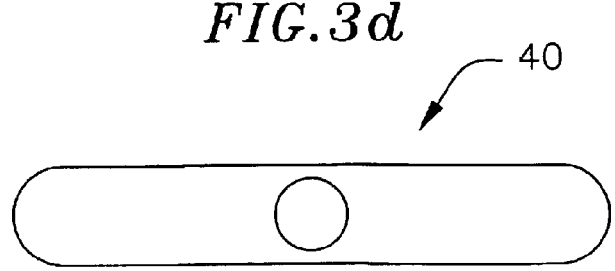
FIG. 3d is a front view of an embodiment of an alignment handle according to the second embodiment of the invention.
Figure 4A:
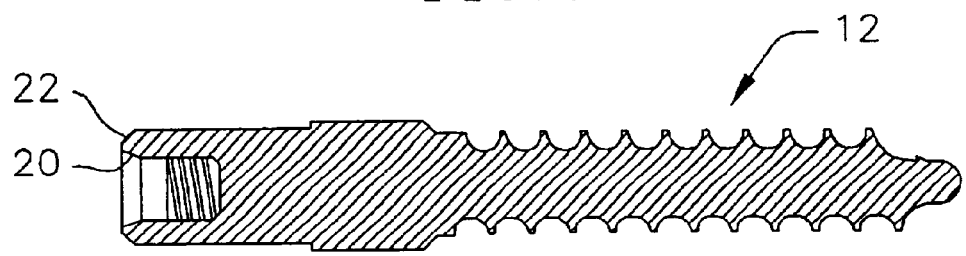
FIG. 4a is a side view and partial cross section of an embodiment of a pedicle screw according to a third embodiment of the invention.
Figure 4B:
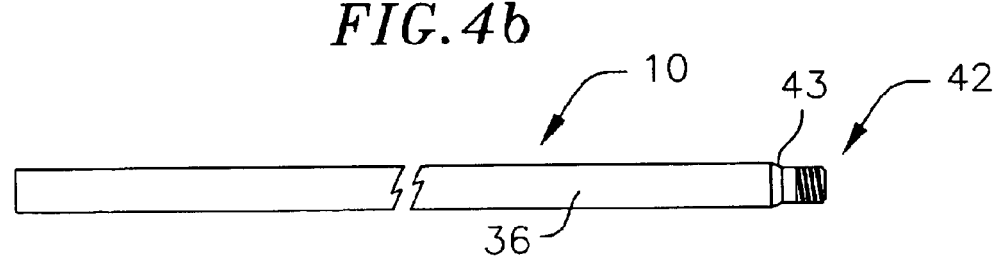
FIG. 4b is a side view of an embodiment of an alignment rod according to the third embodiment of the invention.
Figure 4C:
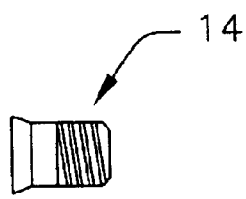
FIG. 4c is a side view of a detail of the tip section of an embodiment of an alignment rod according to the third embodiment of the invention.
Figure 4D:
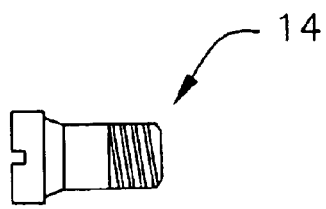
FIG. 4d is a side view of an embodiment of a filler screw according to the third embodiment of the invention.
Figure 5A:
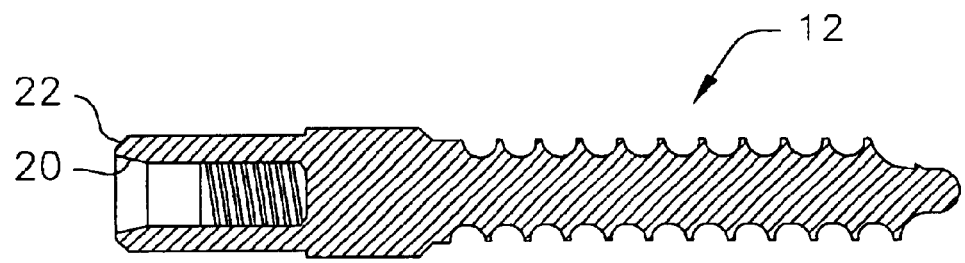
FIG. 5a is a side view and partial cross section of an embodiment of a pedicle screw according to a fourth embodiment of the invention.
Figure 5B:
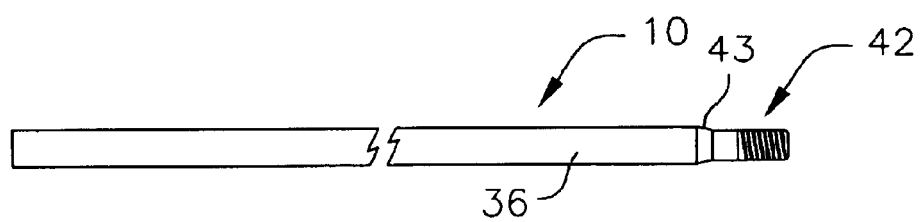
FIG. 5b is a side view of an embodiment of an alignment rod according to the fourth embodiment of the invention.
Figure 5C:
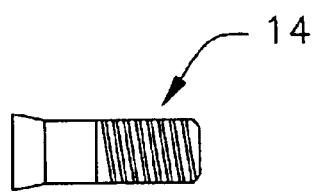
FIG. 5c is a side view of a detail of the tip section of an embodiment of an alignment rod according to the fourth embodiment of the invention.
Figure 5D:
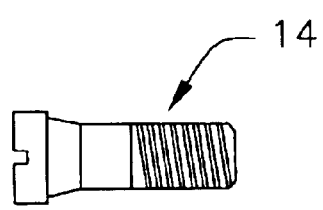
FIG. 5d is a side view of an embodiment of a filler screw according to the fourth embodiment of the invention.

The present invention relates generally to a method and apparatus for aligning and fixing vertebral bodies. More specifically, the present invention is directed to a system and method to allow a surgeon to accurately manipulate and align vertebral bodies using removable alignment rods attached to pedicle screws and to enable the installation of fixation system hardware while the alignment rods are still in place.

As shown in FIGS. 1 to 6, the vertebral alignment system of the current invention consists potentially of three main components: alignment rods 10, cannulated pedicle screws 12, and, optionally, filler plugs 14. In these embodiments, the alignment rod 10 may be inserted and fixed within the pedicle screw 12 through any suitable means.

For example, in various embodiments, the pedicle screw 12 as shown in FIGS. 1a, 2d, 3b, 4a and 5a, is partially cannulated to form a recess 16 and the recess is partially threaded 18. In these embodiments, the recess 16 of the pedicle screw 12 comprises an identical, but reversed image of the alignment rod 10, including threads 18, a counterbore 20 and a flat 22, which conform with that of the alignment rod 10. In these embodiments the alignment rod 10 may (FIGS. 1c, 2b and 3a) or may not (FIGS. 4b and 5b) include a probe portion 24 at the tip of the alignment rod 10.

Although the embodiments of the invention discussed in FIGS. 1 to 5, above, all utilize a threaded mechanism to affix the alignment rod 10 within the recess 16 of the pedicle screw 12, it should be understood that any fixation mechanism may be utilized in the present invention. In one alternative embodiment, shown in FIG. 6, a compression fitting is utilized to affix the alignment rod 10 within the pedicle screw 12. In this embodiment, the alignment rod 10 is cannulated and further comprises a slidable internal shaft 26 running the length of an alignment rod bore 27, and a set of spring-loaded ball bearings 28 compressed within the body of the alignment rod 10 opposite a plurality of engaging openings 30 dimensioned such that a portion of the ball bearings 28 may be extended outside the body of the alignment rod 10, but such that the remainder of each of the ball bearings 28 is fixedly held therein. In this embodiment, the recess 16 of the pedicle screw 12 comprises an identical, but reversed image of the alignment rod 10, including a plurality of anchor receptacles 32 designed to receive the extended ball bearings 28, a counterbore 20 and a flat 22, which conform with that of the alignment rod 10. Although this embodiment only shows an alignment rod 10 including a probe portion 24 at its distal tip (FIG. 6b), it should be understood that the alignment rod need not possess a probe.

Figure 6A:
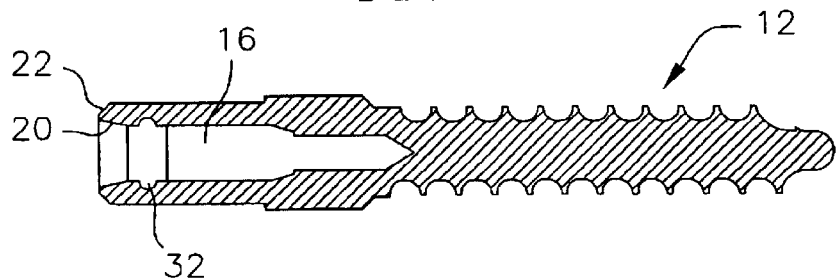
FIG. 6a is a side view and partial cross section of an embodiment of a pedicle screw according to a fifth embodiment of the invention.
Figure 6B:
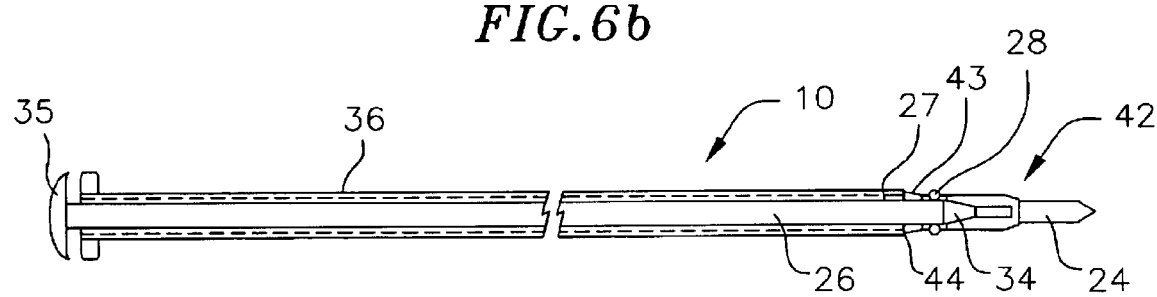
FIG. 6b is a side view of an embodiment of an alignment rod according to the fifth embodiment of the invention.
Figure 6C:
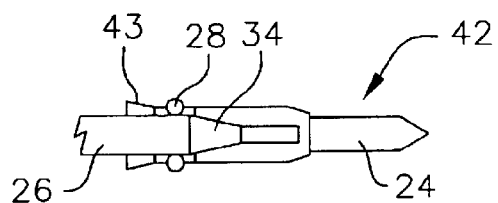
FIG. 6c is a side view of a detail of the tip section of an embodiment of an alignment rod according to the fifth embodiment of the invention in an engaged position with the pedicle screw.
Figure 6D:
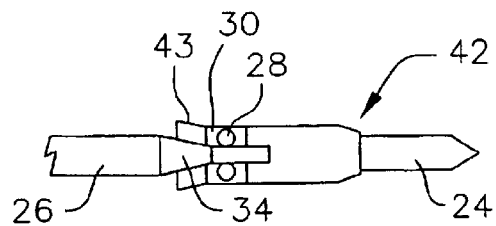
FIG. 6d is a side view of a detail of the tip section of an embodiment of an alignment rod according to the fifth embodiment of the invention in a disengaged position with the pedicle screw.
Figure 7A:
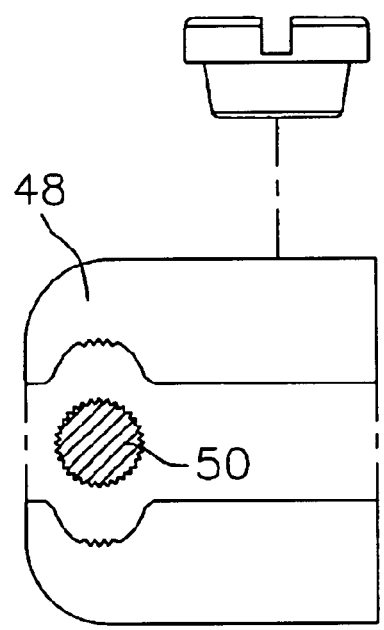
FIG. 7a is a side view of an embodiment of fixation hardware according to the invention.
Figure 7B:
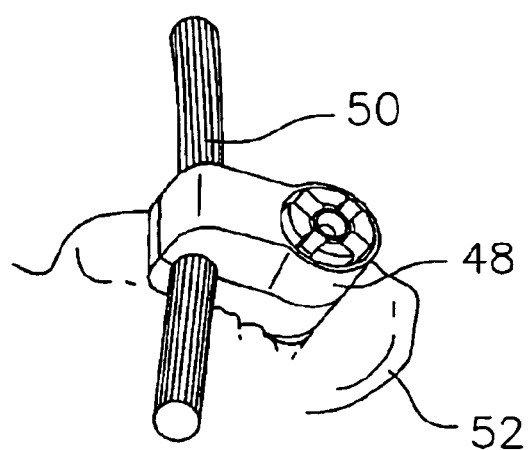
FIG. 7b is a top view of an embodiment of fixation hardware according to the invention.
Figure 7D:
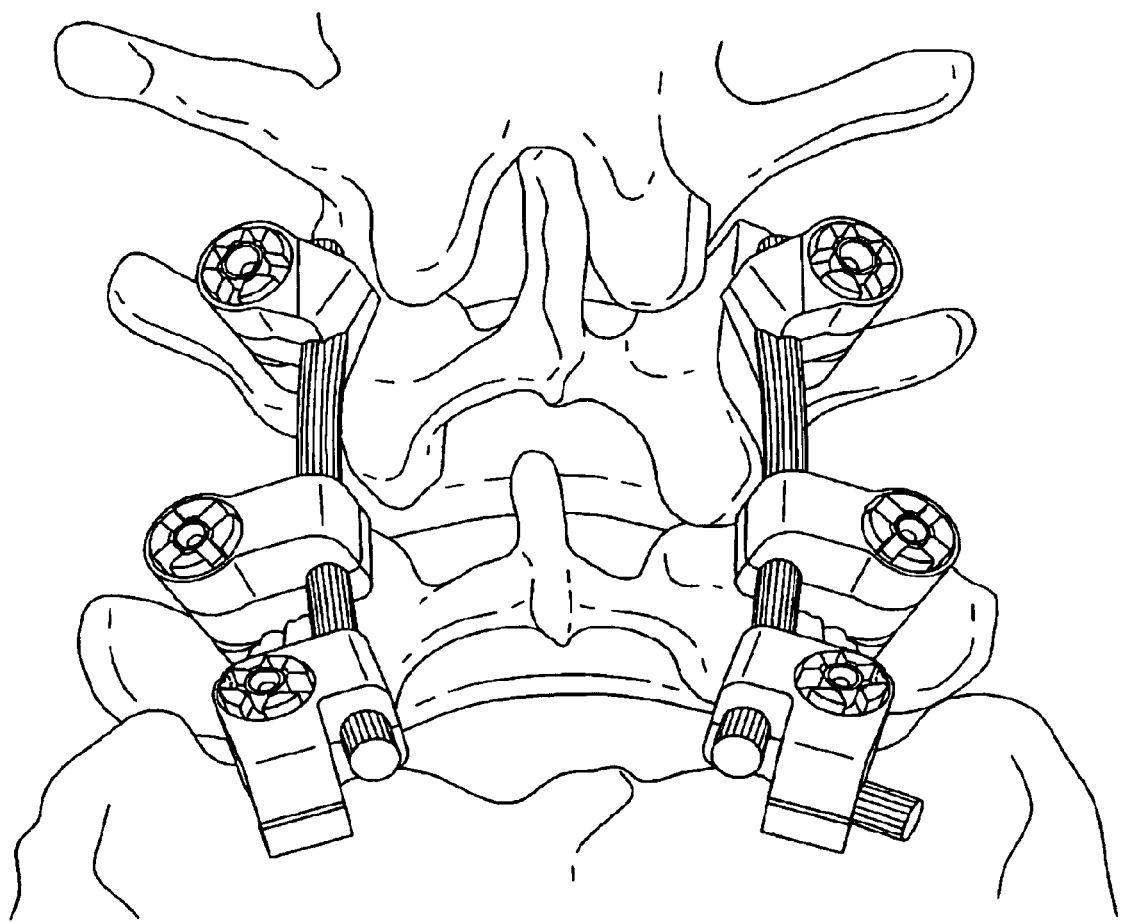
FIG. 7d is a top view of an embodiment of fixation hardware according to the invention.

As shown in FIGS. 6c and 6d, during operation, the alignment rod 10 is positioned within the recess 16 of the pedicle screw 12 such that the ball bearings 28 are positioned opposite the anchor receptacles 32. The internal shaft 26 is then pressed into the alignment rod bore 27 such that the distal tip 34 of the shaft 26 presses against the inner surfaces of the ball bearings 28 forcing the ball bearings through the engaging openings 30 into the anchor receptacles 32, thus fixing the alignment rod 10 within the pedicle screw 12. In such an embodiment, the internal shaft may further comprise a handle 35 and a locking mechanism for locking the compression fitting into place.

Although a compression fitting embodiment is discussed above, it should be understood that any method of attaching the alignment rod within the pedicle screw may be utilized, such as, for example a "bayonet" or "twist and lock" style connector such as that found in coaxial cable.

Regardless of the mechanism chosen to attach the alignment rod within the pedicle screw, the diameter and depth of the recess is designed to mate with that of the alignment rod threads and probe. In all of the above discussed embodiments, the pedicle screw is preferably made from surgical grade titanium.

The alignment rods 10, as shown in FIGS. 1c, 2b, 3a, 4b, 5b and 6b are sized to allow fixation hardware to slide down the shaft 36 of the rod, which in turn allows the rod to remain in place until fixation hardware is placed and tightened. The rod 10 includes threads 38 at the distal end, to allow for a T-Handle 40, knob or alignment/stabilization frame to be attached. These threads 38 may also be used for the attachment of a screwdriver-type handle and be utilized for the installation of the pedicle screws 12 into the vertebral bodies. As discussed above, the rods 10 also preferably have a connecting device, such as, a threaded portion or a compression fitting at the proximal end 42, to mate with a cooperating fitting in the recess 16 of the pedicle screw 12.

As discussed above, the rods 10 may include a reduced diameter "probe" 24 extending beyond the connecting device. In these embodiments, the probe 24 allows for guidance of the alignment rod 10 into the pedicle screw 12, provides additional rod strength and shifts the center of rotation further into the pedicle screw. The probe portion 24 of the rod 10 may come in various lengths and diameters, as shown in FIGS. 1 and 2 versus FIG. 3, and may or may not be tapered.

The rod also includes a conical tip and counterbore 43 between the connecting device and the handle portion of the rod, which mates with a similar counterbore and countersink 20 inside the pedicle screw 12. This feature allows the rod 10 to seat positively to the pedicle screw 12 and provides additional support between the rod and screw. The rod 10 also includes a flat 44 that provides for positive mating of the rod to the top of the pedicle screw. The rods 10 will preferably vary in length between approximately, 4 and 12 inches although other sizes may be used. The selection of the rod length will be based upon the size of the patient and access to the surgical site.

The filler plug 14, as shown in FIGS. 1b, 2c, 3c, 4d and 5d, is shaped identically to that of the end of the alignment rod 10, but is much shorter. The plug 14 is optionally placed into the pedicle screw 12 after the hardware has been tightened and the alignment rod 10 is removed. At the option of the surgeon, the alignment rod 10 may also be severed immediately above the pedicle screw 12, leaving the connector portion of the alignment rod 10 in place to act as a filler plug. The purpose of the filler plug 14 is to provide additional screw strength, where the wall diameter has been reduced by the threads and probe recess. The filler plug 46 is an optional component, but if used, will remain in the body with the pedicle screw implant. In those embodiments in which a separate filler plug 14 is attached to the pedicle screw 12, the top of the filler plug will preferably have a flat or crossed recess, or have a hex or allen wrench style cap and will be installed and tightened with a similarly shaped surgical screwdriver.

In addition to these basic components, fixation hardware, such as, for example, that shown in FIGS. 7a to 7d, would also be provided to fix the spine into the desired alignment. The fixation hardware may comprise clamps 48, which are designed to slide down the alignment rod 10 and mate with top or side of the cannulated pedicle screw at an external connector 46, such as a external threaded portion of the screw as shown in FIGS. 1a, 2b, 3b, 4a, 5a, and 6a, bendable fixation rods 50 or plates, which run between the clamps on the various pedicle screws 12 attached either to different vertebral bodies 52 or at different points on a single vertebral body, and bolts, also designed to slide down the alignment rod and mate with the clamps such that the clamps 48 can be tightened onto and fix the fixation rods 50 into place.

All of the above components, including the fixation hardware can be made of any suitable surgical material, such as, for example, stainless steel or titanium.

Figure 8:
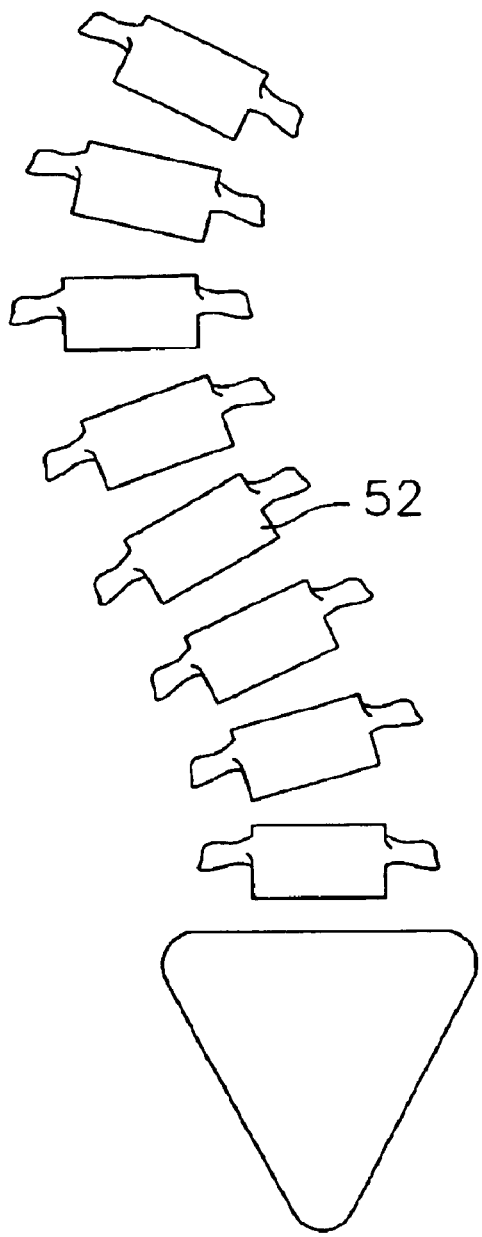
FIG. 8 is a schematic view of the deformity caused by Scoliosis.
Figure 9:
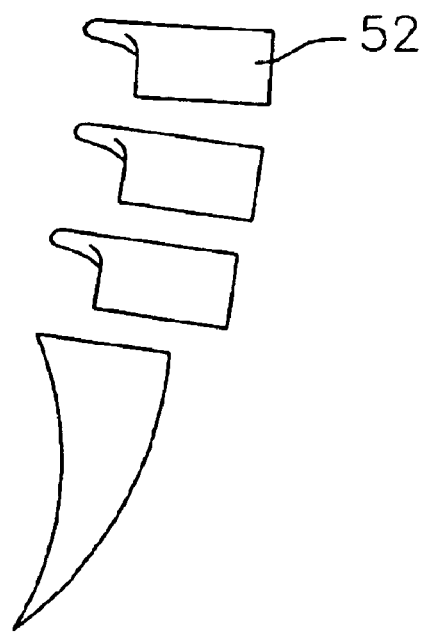
FIG. 9 is a schematic view of the deformity caused by Spondylolisthesis.
Figure 10:
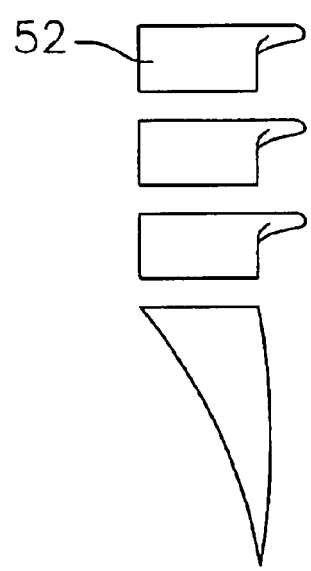
FIG. 10 is a schematic view of the deformity cased by Kyphosis
Figure 11:
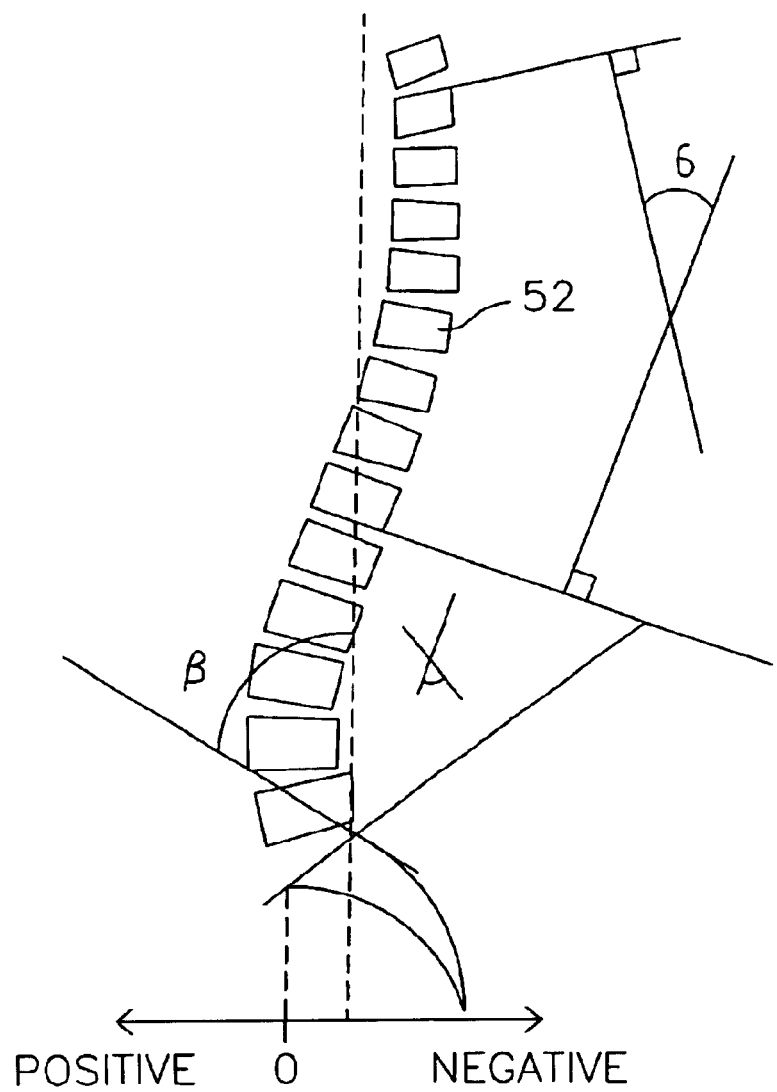
FIG. 11 is a schematic view of the desired lordosis of a thoracic and a lumbar spine.

For an exemplary procedure, two pedicle screws, two alignment rods and optionally, two filler plugs along with the appropriate fixation hardware are used at each vertebral level. The number of components used would depend upon the spinal abnormality and the number of vertebral bodies, or levels to be aligned and fused. Examples of some common spinal abnormalities and normal spinal curvature are depicted in FIGS. 8 to 11. Scoliosis, in which, on a frontal or anterior view, the spine is angled or curved to the left or right, in some cases there may also be rotation of each individual segment to the left or right, as shown in FIG. 8; Spondylolisthesis, most common in the lumbar region, in which a spinal segment has slipped forward over the underlying spinal segments, as shown in FIG. 9; and Kyphosis, or flat back syndrome, in which there is a loss of normal sagittal curvature in the lumbar spine, as depicted in FIG. 10. A normal spinal curvature or lordosis is depicted for comparison in FIG. 11.

FIGS. 12a to 13b show a spinal alignment and fixation procedure utilizing the vertebral alignment apparatus and system described above. First a cannulated pedicle screw 12 according to the invention would be placed into the left and right pedicle 56 of the individual vertebra 52. An alignment rod 10, as described above, would then be inserted into the cannulated pedicle screw 12 and secured into the barrel of the cannulated pedicle screw. After this procedure, the alignment rod 10 extends above the screw 12 for a distance preferably between 4 to 12 inches, however any extension distance may be used depending upon the lever force the surgeon desires. Different size rods allow the surgeon to apply appropriate forces and lever to the spinal vertebral body. In one embodiment, the alignment rods 10 also have threaded ends 38 at the tops of the alignment rods permitting the surgeon to screw T-handles 40 (See FIGS. 12a and 13b), or other appropriate manipulation devices, such as for example, alignment cages to the ends of the alignment rods. The alignment rods 10 are then used to manipulate and align the vertebral body 52 to the desired angle and position according to known techniques, after which the position is verified by visualization and by X-ray. The surgeon has the capacity to use the alignment rods 10 that are inserted into the hollow pedicle screw 12 because there is ligamentous laxity to each individual vertebral segment 52. This ligamentous laxity allows the surgeon to manipulate the vertebral body. For example, the surgeon would rotate or tilt the vertebral body to correct scoliosis, pull or push the vertebral body to correct spondylolisthesis or retrolisthesis, tilt the vertebral body to improve sagittal alignment to promote lumbar lordosis and reduce flat back syndrome. Compression and distraction can also be applied to these points as well to promote correction of deformity.

Figure 12A:
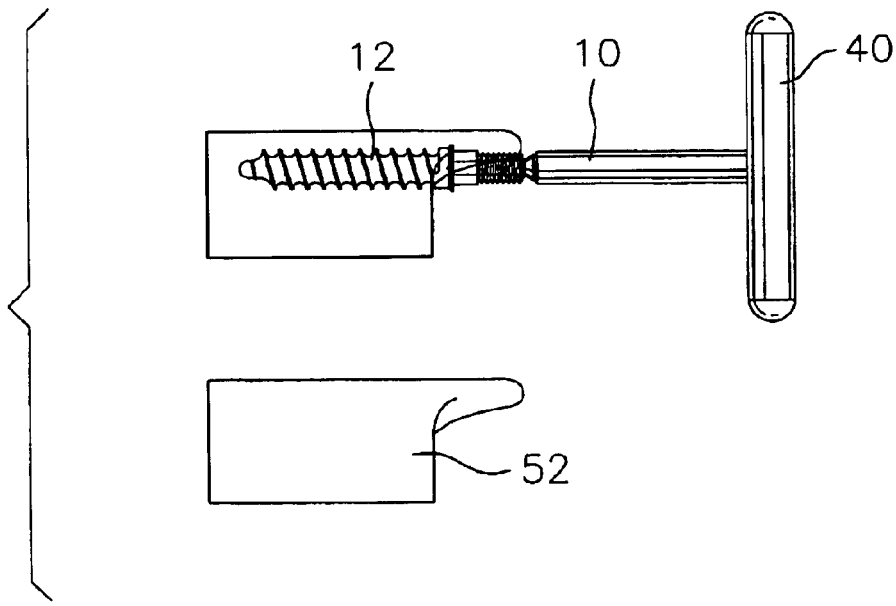
FIGS. 12a and 12b are cross-sectional views of the placement of an embodiment of alignment rods into an embodiment of pedicle screws according to the invention.
Figure 12B:
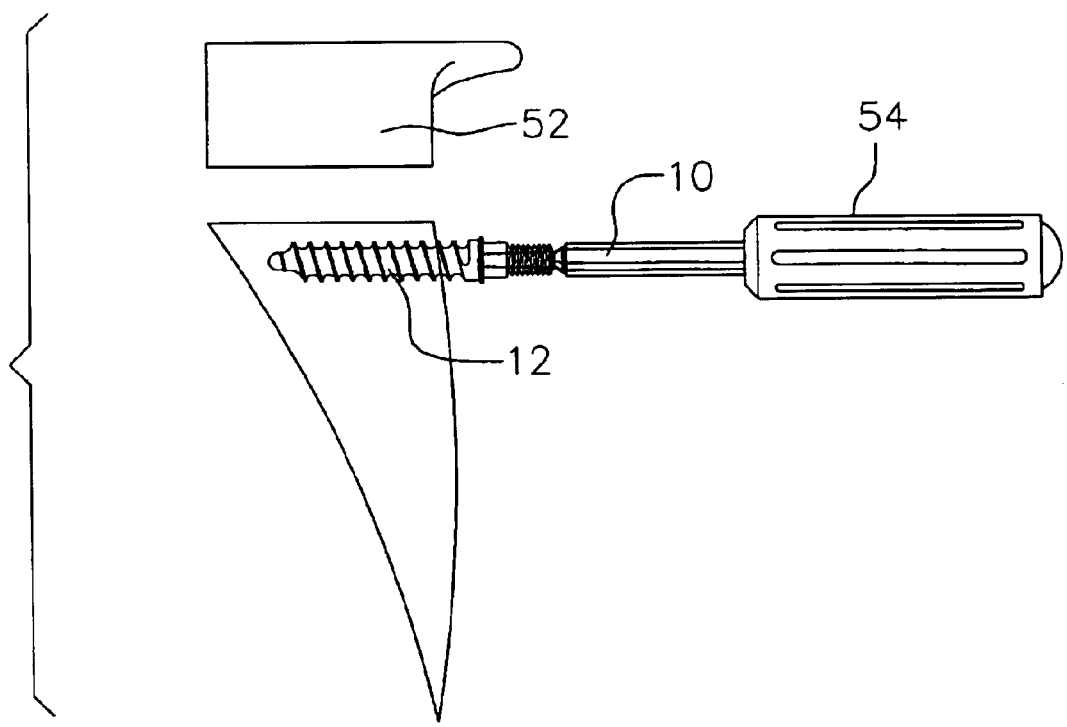
Figure 13A:
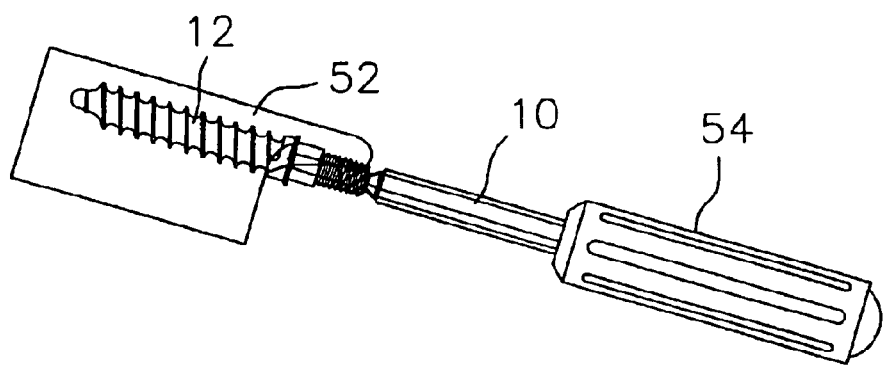
FIGS. 13a and 13b are schematic views of the manipulation and alignment of the spine utilizing an embodiment of the vertebral alignment system according to the invention.
Figure 13B:
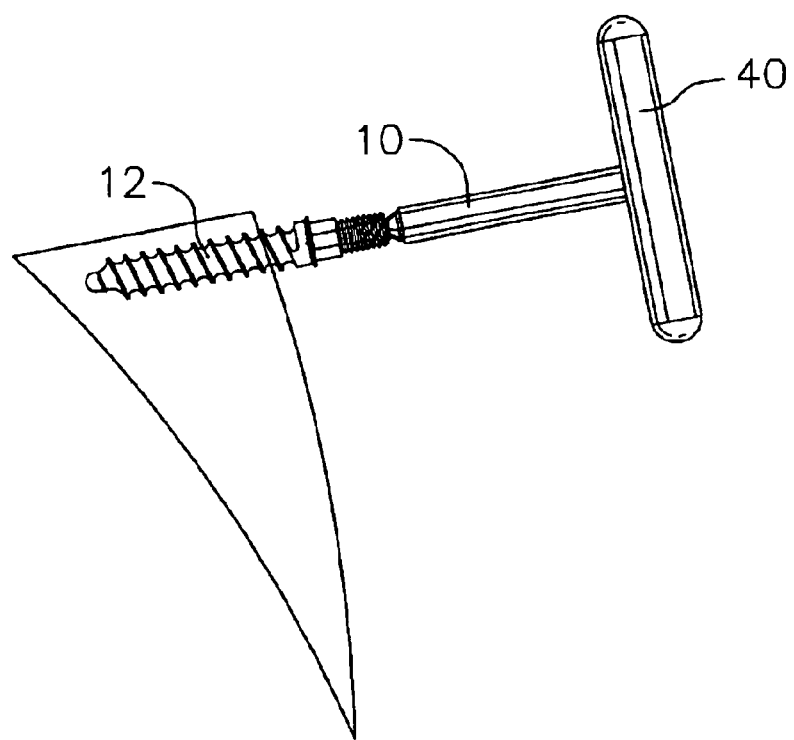

Alternatively, after the vertebral body 52 has been tapped and prepared for the implantation of the pedicle screw 12, the vertebral alignment system according to the present invention enables the surgeon to install the pedicle screw 12 by connecting the screwdriver handle 54 to the distal end of the alignment rod 10, placing the pedicle screw 12 on the proximal end of the alignment rod 10 and implanting the pedicle screw (See FIGS. 12b and 13a). Once the pedicle screw 12 is secured into the vertebral body 52, the surgeon may utilize the pedicle screw to navigate the spinal segment and correct the spinal deformity and not just as a point of attachment for the fixation hardware.

Once the surgeon has manipulated the vertebral bodies into the proper, or desired, alignment, the fixation hardware is slipped down the shaft of the alignment rod 10. The fixation hardware may, for example, comprise clamps 48 and rods 50 that mate with the cannulated pedicle screws 12 to allow for fixation of the desired vertebral alignment. In one possible method, the surgeon first aligns the vertebral bodies and then the clamps are placed over the alignment rods onto the pedicle screw or to the sides of the pedicle screws. Fixation rods or plates are then bent to the desired alignment and are then placed over the alignment rods or along the sides of the alignment rods and onto the clamps. Bolts are then secured onto these clamps, either over or at the side of the alignment rod. A specially designed cannulated screwdriver is slid down the shaft of the alignment rod and the bolts and clamps are then tightened over the fixation rods and the spine is then fixed, or held, in the alignment desired by the surgeon.

In an alternative method, the clamps and bolts are slid down the alignment rod to mate with the pedicle screw prior to alignment, but not tightened. The surgeon would then manipulate the vertebral bodies into the proper, or desired, alignment and the fixation rods or plates would then be bent to the desired alignment and placed into the already positioned clamps and the bolts then secured. The surgeon may alternatively use an iterative process to align the fixation rods or plates into position so that the vertebral bodies do not have an opportunity to slip into a misaligned conformation. In this iterative process, the fixation rods would be aligned and clamped multiple times before placing the spine into the proper conformation. In another alternative method designed to prevent a misalignment of the aligned spine, a clamp, cage framework, surgical band or other suitable device may be utilized to hold the alignment rods in place once the surgeon has aligned them and while the fixation rods or plates are being adjusted and clamped to the pedicle screws.

Regardless of the method used to tighten the clamps on the fixation rods or plates, once the bolts have been tightened, the screwdriver is then removed and the alignment rods are detached from the inside of the pedicle screw. A filler plug, as described above, is then, optionally, inserted into the pedicle screw and tightened making the pedicle screw whole. Optionally the alignment rod may also be severed immediately above the pedicle screw leaving a portion of the alignment rod in place to act as a filler plug. The operation site is then closed per normal surgical procedures.

Figure 14A:
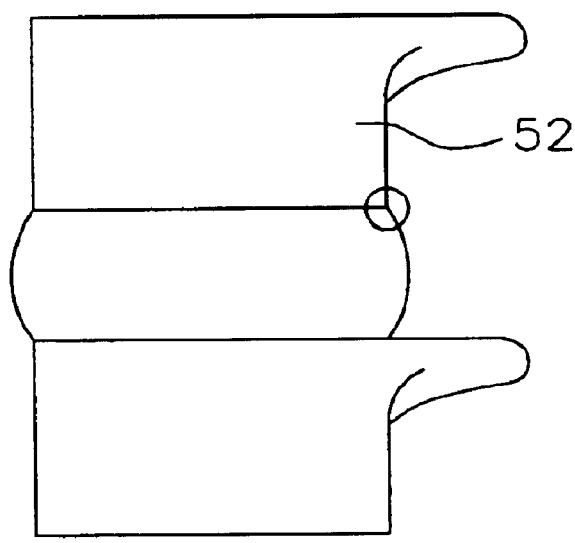
FIGS. 14a and 14b are schematic views of the point of rotation of the vertebral alignment system according to the invention.
Figure 14B:
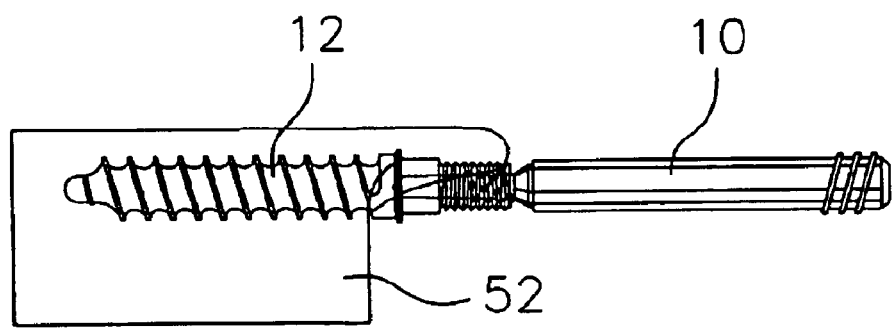

It is important to note that the instantaneous center of rotation of a spinal segment is in the posterior lateral corner of the vertebral body. The alignment rod 10 of the present invention is designed to fit into the pedicle screw at closely the approximate point 56 at which the center of rotation occurs in the vertebral segment 52, as shown in FIGS. 14a and 14b. This allows the surgeon to apply force as a lever to the pedicle screw and use the lever of the pedicle screw to alter the vertebral body's position at its instantaneous center of rotation. Predictably, this ability to mate the lever to the screw inside the pedicle allows the surgeon maximum ability to correct deformities.

One important example of this improved ability to correct deformities is realized in procedures involving correcting improper lumbar lordosis. Lumbar lordosis refers to the sagittal alignment of the spine in most disorders, due to degeneration of the disc or spondylolisthesis, lumbar lordosis is incrementally lost in the spine. Most current fusion methods do not improve lordosis. In fact, most fusion methods reduce lumbar lordosis.

There are many articles relating the deleterious effects of introgenic loss of lumbar lordosis after spinal instrumentation in the distal lumbar spine which leads to flat back syndrome. In short, there is a reciprocal balance between the curves of surgical lordosis, thoracic kyphosis and lumbar lordosis which allows efficient energy of absorption of the spinal column and increased efficiency of spinal musculature.

In effect, lordosis is promoted by placing the pedicle screws in the vertebral body and using the alignment rod to lever the vertebral bodies so the anterior margin of the vertebral body in question, i.e., L4 to the sacrum, increases in distance as the lever arms are used. This improves the instantaneous center of rotation at each adjacent segment and reduces the stress of the vertebral body at the adjacent unfused segments. This appears to be most important for reducing stress at these levels and therefore reducing the potential for accelerated degeneration. The technique represents a new advancement in the art of spinal surgical correction.

Although specific embodiments are disclosed herein, it is expected that persons skilled in the art can and will design alternative vertebral alignment systems that are within the scope of the following claims either literally or through substantial equivalents. For example, although the above discussion has described the use of an alignment rod and fixation hardware with a pedicle screw only, it should be understood that any device suitable for anchoring fixation hardware to a vertebral body, such as by way of example clamps, may be utilized with the present invention provided the anchor device is cannulated to allow the insertion of an alignment rod therein, and provided the body of the anchor device is so designed as to allow the top loading of fixation hardware down the alignment rod and onto the body of the anchor device.

What is claimed is:

1. A vertebral alignment/fixation system comprising:
    at least one elongated spinal adjustment device;
    at least one vertebral alignment/fixation assembly comprising:
        a screw comprising an elongated, partially cannulated shaft defining an axially arranged inner screw chamber and a screw axis, an axial opening being arranged at a proximal end of the shaft providing access to the inner screw chamber of the shaft and a tapered tip arranged at the distal end of the shaft, and wherein a distal end of the shaft is externally threaded for driving the screw into bone and wherein the proximal end of the shaft further comprises an anchor mechanism for attachment of at least one piece of fixation hardware, and
        an alignment rod comprising an elongated shaft with an engaging portion arranged at the distal end of the shaft designed to insert into the axial opening and cooperatively engage the inner screw chamber of the shaft, and a elongated portion arranged at the proximal end of the shaft, the elongated portion of the alignment rod having an outer diameter less than or equal to that of the screw;
    at least one piece of fixation attachment hardware designed to slide down the alignment rod and cooperatively engage the proximal anchor mechanism of the screw such that the at least one fixation attachment is fixedly attached thereto, the at least one fixation attachment further being designed to anchor the at least one spinal adjustment device in place.

2. A vertebral alignment/fixation system as described in claim 1, further comprising a filler plug, mateable with said inner screw chamber, the plug being designed to lockingly engage within and fill the inner screw chamber.

3. A vertebral alignment/fixation system as described in claim 1, wherein the spinal adjustment device is chosen from the group consisting of: plates, rods, clamps, crosslinks and wires.

4. A vertebral alignment/fixation system as described in claim 1, wherein the fixation attachment is chosen from the group consisting of: clamps, bolts and nuts.

5. A vertebral alignment/fixation system as described in claim 1, wherein the inner screw chamber of the shaft and the engaging portion of the alignment rod further comprise engagement mechanisms designed to cooperatively engage to lockingly hold the engaging portion of the alignment rod within the inner screw chamber of the screw shaft.

6. A vertebral alignment/fixation system as described in claim 5, wherein the engagement mechanism is selected from the group consisting of: a threaded fitting, a compression fitting, and a twist and lock mechanism.

7. A vertebral alignment/fixation assembly as described in claim 1, wherein the elongated portion of the alignment rod is threaded to receive a threaded attachment.

8. A vertebral alignment/fixation assembly as described in claim 7, wherein the elongated portion of the alignment rod is threaded to receive the threaded attachment consisting of either a T-type handle or a screwdriver-type handle.

9. A vertebral alignment/fixation system as described in claim 1, wherein the system components are made of stainless steel.

10. A vertebral alignment/fixation method comprising:

providing a vertebral alignment/fixation system as described in claim 1;

driving the screw into a vertebral body;

inserting the alignment rod into the inner screw chamber of the screw;

aligning the vertebral body with the alignment rod;

sliding a piece of fixation attachment hardware down the alignment rod onto the screw;

tightening piece of fixation attachment hardware onto the screw; and attaching a spinal adjustment device onto the fixation attachment hardware to fix the vertebral body in the chosen alignment.

11. A vertebral alignment/fixation method comprising utilizing a vertebral alignment/fixation system as described in claim 1 to align at least one vertebral body.

12. A vertebral alignment/fixation method comprising utilizing a plurality of vertebral alignment assemblies as to align at least one vertebral body, wherein each of the vertebral alignment assemblies comprises:

a screw comprising an elongated, partially cannulated shaft defining an axially arranged inner screw chamber and a screw axis, an axial opening being arranged at a proximal end of the shaft providing access to the inner screw chamber of the shaft and a tapered tip arranged at a distal end of the shaft, and wherein the distal end of the shaft is externally threaded for driving the screw into bone and wherein the proximal end of the shaft further comprises an anchor mechanism for attachment of at least one piece of fixation attachment hardware; and an alignment rod comprising an elongated shaft with an engaging portion arranged at a distal end of the shaft designed to insert into the axial opening and cooperatively engage the inner screw chamber of the shaft, and an elongated portion arranged at a proximal end of the shaft, the elongated portion of the alignment rod having an outer diameter less than or equal to that of the screw.

* * * * *